(12) United States Patent
Atwood et al.

(10) Patent No.: US 8,329,891 B2
(45) Date of Patent: Dec. 11, 2012

(54) METHODS FOR IDENTIFYING AGENTS THAT INHIBIT CELL MIGRATION, PROMOTE CELL ADHESION AND PREVENT METASTASIS

(75) Inventors: Craig S. Atwood, Madison, WI (US); Sivan Vadakkadath Meethal, Madison, WI (US)

(73) Assignee: Genremedy LLC, Cleveland, OH (US)

( * ) Notice: Subject to any disclaimer, the term of this patent is extended or adjusted under 35 U.S.C. 154(b) by 0 days.

(21) Appl. No.: 13/366,692

(22) Filed: Feb. 6, 2012

(65) Prior Publication Data

US 2012/0190588 A1 Jul. 26, 2012

Related U.S. Application Data

(62) Division of application No. 12/709,897, filed on Feb. 22, 2010, now Pat. No. 8,110,355.

(60) Provisional application No. 61/154,251, filed on Feb. 20, 2009.

(51) Int. Cl.
*C07H 21/02* (2006.01)
*C07H 21/04* (2006.01)
*C12Q 1/68* (2006.01)

(52) U.S. Cl. ................ 536/24.5; 435/6.1; 435/91.1

(58) Field of Classification Search .............. 536/24.5; 435/6, 91.1
See application file for complete search history.

(56) References Cited

OTHER PUBLICATIONS

Liu et al. Transforming Growth Factor Beta2, but not Beta1 and Beta3, is Critical for Early Rat Lung Branching. Developmental Dynamics, 2000 vol. 217:343-360.*
D. Simon et al., "Activin Receptor Signaling Regulates Prostatic Epithelial Cell Adhesion and Viability," Neoplasia 11-365-376, 2009.

* cited by examiner

*Primary Examiner* — Terra Cotta Gibbs
(74) *Attorney, Agent, or Firm* — Baker & Hostetler LLP

(57) ABSTRACT

Disclosed are methods for identification of agents that modulate cell attachment, cell migration and cell viability. Cancer and primary cells adhered to a matrix are treated with agent(s) that modulate ActRII signaling and cell adhesion. Agents are tested that modulate cell adhesion, detachment, invasion and viability. Agents that modulate the expression, phosphorylation, function and translocation of ActRII signaling pathway members also can predict agents that modulate cell adhesion, detachment, invasion and viability. The methods have utility in identifying agents that prevent cancer cell metastasis, wound dehiscence, aortic dissection and aid retina attachment and skin replacement and fertility.

19 Claims, 6 Drawing Sheets

ActRII signaling pathway linked to disintegrin expression and function

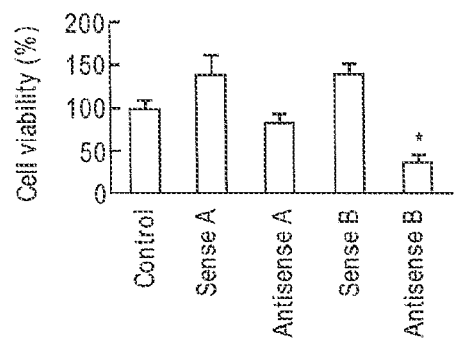
FIG. 3A
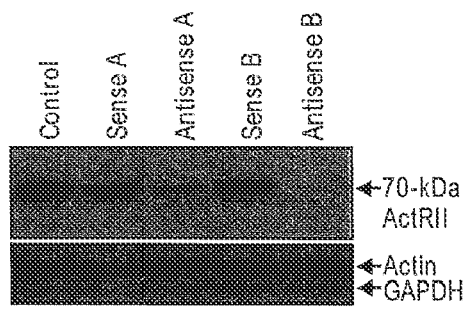
FIG. 3B
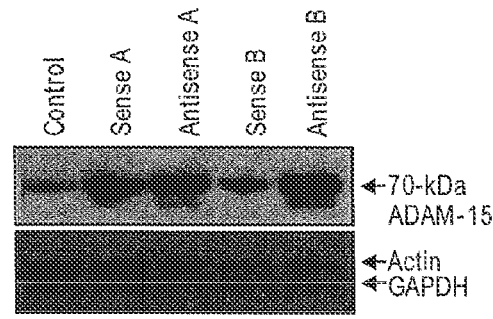
FIG. 3C
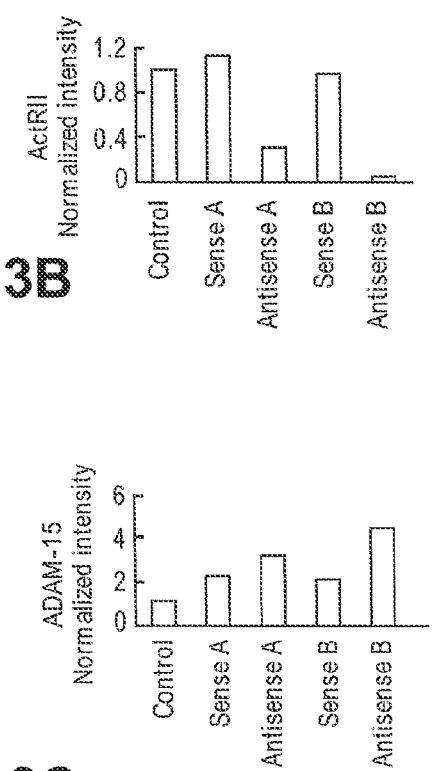

METHODS FOR IDENTIFYING AGENTS THAT INHIBIT CELL MIGRATION, PROMOTE CELL ADHESION AND PREVENT METASTASIS

CROSS-REFERENCE TO RELATED APPLICATIONS

This application is a divisional of and claims priority to U.S. patent application Ser. No. 12/709,897, now, U.S. Pat. No. 8,110,355, entitled "Method for Identifying Agents that Inhibit Cell Migration, Promote Cell Adhesion and Prevent Metastasis," filed Feb. 22, 2010, which claims priority to provisional U.S. Patent Application filed Feb. 20, 2009, having a Ser. No. 61/154,251, the disclosures of which are hereby incorporated by reference in their entireties.

FIELD OF THE INVENTION

The invention relates to an assay that can identify agents that inhibit cell migration, promote cell adhesion and prevent metastasis.

BACKGROUND OF THE INVENTION

Metastasis of cells from a primary tumor in mammals leads to the spread of cancer to other tissues of the body (1-3). The spread of metastases may occur via the blood or the lymphatics or through both routes. Cancer cell metastasis commonly occur in lungs, liver, brain, and the bones. These secondary aggressive cancers lead to organ dysfunction and ultimately death (Metastatic Cancer: Questions and Answers". National Cancer Institute). To date, there are few effective treatments for metastatic cancers.

Signaling pathways that promote cell detachment and/or metastasis are largely unknown. However, we have discovered signaling pathways that unexpectedly regulate cell adhesion to the extra-cellular matrix (ECM) are prime candidates for promoting metastasis (4). These pathways may be impacted upon by the many genetic and epigenetic changes as a cell transitions to malignancy, together with microenvironmerital changes such as changes in hormone signaling.

Wound dehiscence is the premature "bursting" open of a wound along surgical suture. It is a surgical complication that results from poor wound healing. Risk factors are age, diabetes, obesity, poor knotting/grabbing of stitches and trauma to the wound after surgery. Agents that promote cell adhesion could speed healing. Retinal detachment is a disorder of the eye in which the retina peels away from its underlying layer of support tissue. Initial detachment may be localized, but without rapid treatment the entire retina may detach, leading to vision loss and blindness. Agents that promote cell adhesion could speed healing. Aortic dissection is a tear in the wall of the aorta that causes blood to flow between the layers of the wall of the aorta and force the layers apart. Aortic dissection is a medical emergency and can quickly lead to death, even with optimal treatment. If the dissection tears the aorta completely open (through all three layers), massive and rapid blood loss occurs. Agents that promote cell adhesion could speed heating. Major skin trauma (e.g. burns, amputation) can be treated with temporary, artificial or autologous skin replacement. Agents that promote cell adhesion could speed healing. Blastocyst attachment to the endometrium of the uterine wall is essential for pregnancy and is a cause of infertility, Agents that promote blastocyst attachment could prevent infertility. Unfortunately, signaling pathways that regulate cell adhesion are largely unknown.

We have identified a pathway, the activin receptor type II (ActRII) signaling pathway, that regulates cell adhesion, Blocking ActRII signaling alters cellular morphology and increases cell detachment. Cell detachment correlates with an increase in the expression of ADAM-15, disintegrin which cleaves integrin molecules (5) and cadherin (6), in this context, it has recently been demonstrated that the expression of ADAM-15 is strongly correlated with the metastatic potential of prostate, breast (7) and pancreatic cancers (8) and is highly up-regulated in aggressive prostate cancer (6). Furthermore, ADAM-15 has been shown to be involved in cell migration and invasion (9, 10). Signal transduction components of the activin signaling pathway are highly down-regulated in prostate cancer (11, 12). In vitro, inhibition of ADAM15 expression in PC-3 cells decreases cell migration and adhesion to specific extracellular matrix proteins, and is accompanied by a reduction in the cleavage of N-cadherin by ADAM15 at the cell surface (6). In patients with hone metastasis from prostate cancer, circulating levels of activin A are significantly higher (13). These findings indicate that ActRII mediates cell adhesion (and viability) via the regulation of ADAM-15 expression and function.

Modulation of ActRII signaling and associated disintegrins can be used to identify drugs that enhance ActRII signaling and promote cell attachment, or inhibit the expression and/or function of disintegrins associated with promoting cell detachment. Accordingly, it is desirable to provide a method, kit, and apparatus for utilizing ActRII signaling and associated disintegrins to identify compounds and conditions capable of modulating adhesion characteristics of cell.

SUMMARY OF THE INVENTION

The foregoing needs are met, to a great extent, by the present invention, wherein in one respect methods and kits for identifying agents that inhibit cell detachment and increase cell attachment, and to the use of such agents to develop methods of preventing, treating or alleviating and/or the symptoms of cancer, and other diseases and conditions is provided. Some examples of such diseases and conditions are described. More specifically, the present invention is directed to the identification of agents that could be used to treat cancer, or other conditions and diseases where cell detachment or migration is detrimental, or where cell adhesion is beneficial. The methods may include detecting, either directly or indirectly, agents that increase ActRII signaling, and/or decrease disintegrin or metalloprotcase expression and/dr function, and prevent cell detachment and cell invasion. Conversely, methods may include detecting, either directly or indirectly, agents that decrease ActRII signaling, and/or increase disintegrin or metalloprotease expression and/or function, and increase cell attachment and cell invasion.

An embodiment of the present invention pertains to a method of identifying an agent to modify cell adhesion. In this method, cells from an animal are adhered to a matrix, cell detachment from a matrix is induced by suppressing ActRII signaling, the agent is introduced, and a change in cell detachment as a result of introducing the agent is measured.

Another embodiment of the present invention relates to a kit to identify an agent to modify cell adhesion. The kit includes a cell growth media, a container having a surface matrix for cell adhesion, and a cell detachment solution having a concentration of an ActRII signaling suppressor sufficient to induce cell detachment.

Yet another embodiment of the present invention pertains to a composition to induce cell detachment comprising a concentration of an ActRII signaling suppressor sufficient to induce cell detachment.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 3 illustrates that anti-ActRII oligonucleotide (antisense P) suppression of ActRII signaling promotes increased ADAM15 expression, increased detachment and decreased viability of prostate cancer cells.

DEFINITIONS

Figure 1:
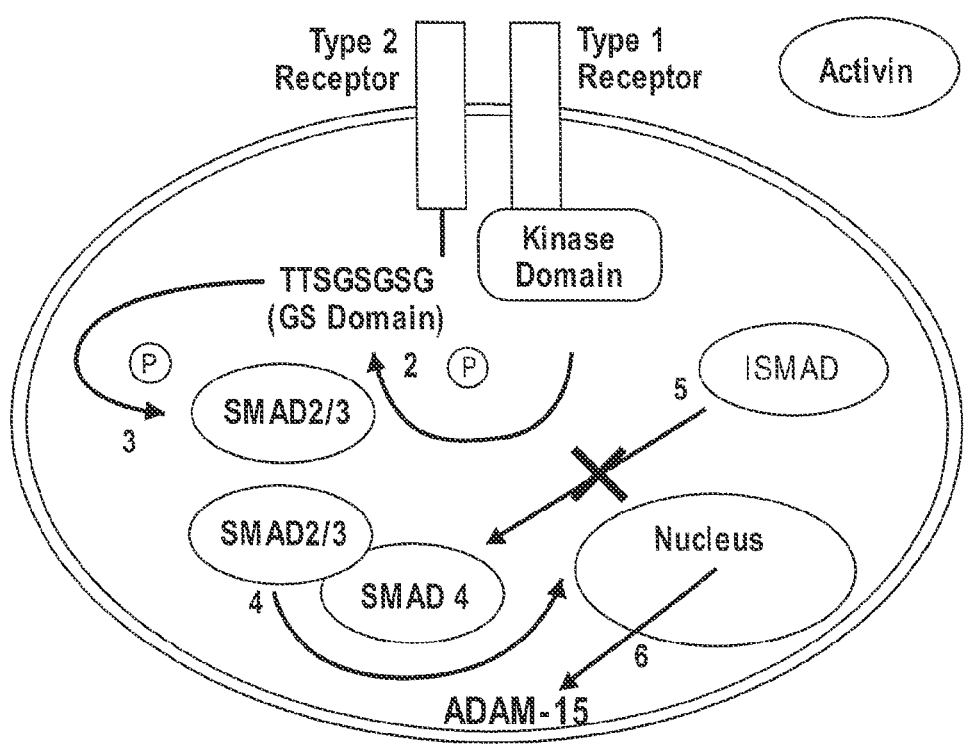
FIG. 1 illustrates the ActRII signaling pathway linked to the expression and function of the disintegrin ADAM15.
Figure 2A:
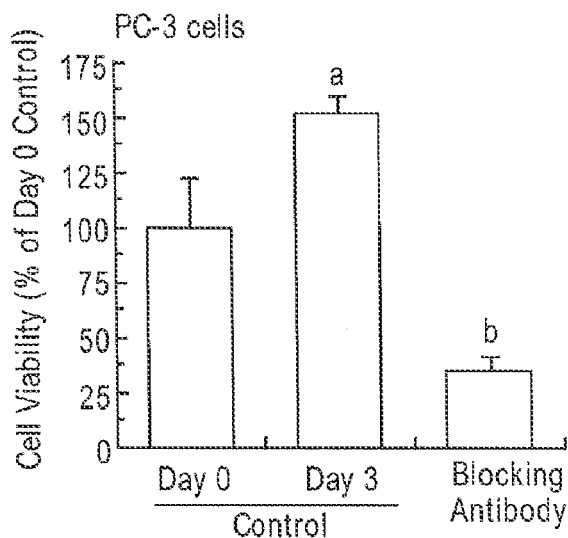
FIG. 2 illustrates that ActRII blocking antibody suppression of ActRII signaling promotes morphological changes, increased detachment and decreased viability of prostate cancer cells.
Figure 2B:
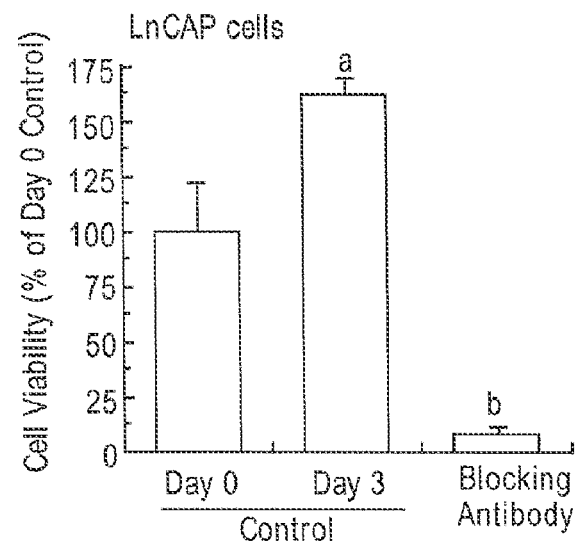
Figure 2B:
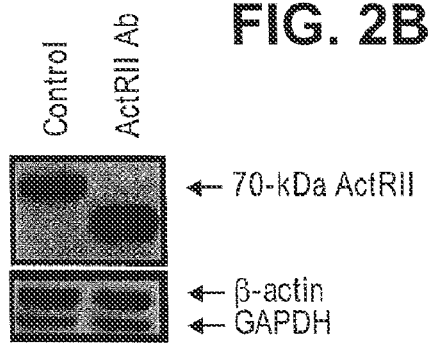
Figure 2C:
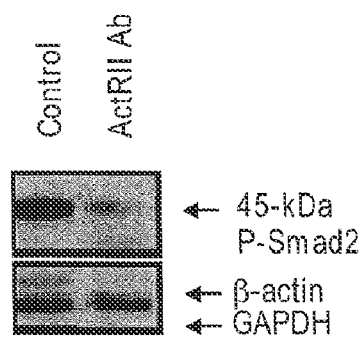
Figure 2D:
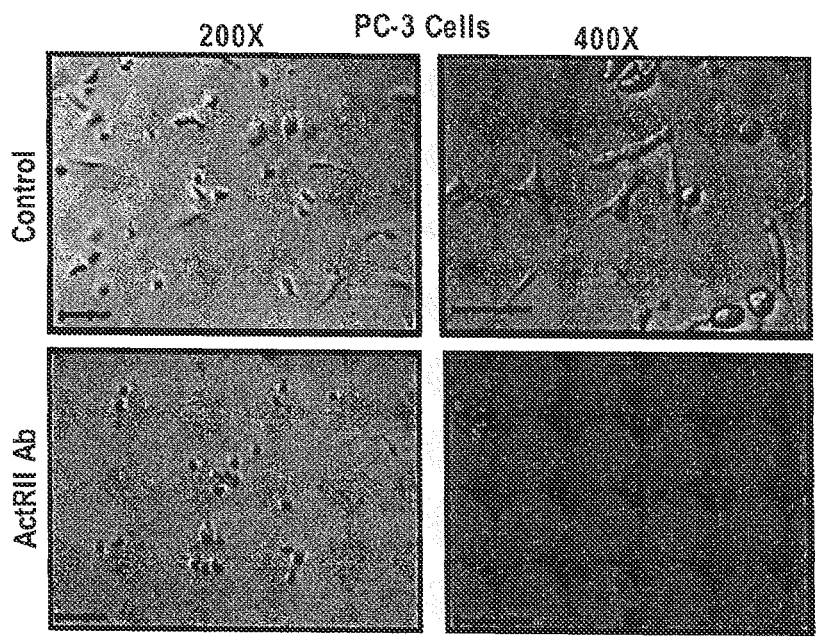
Figure 2E:
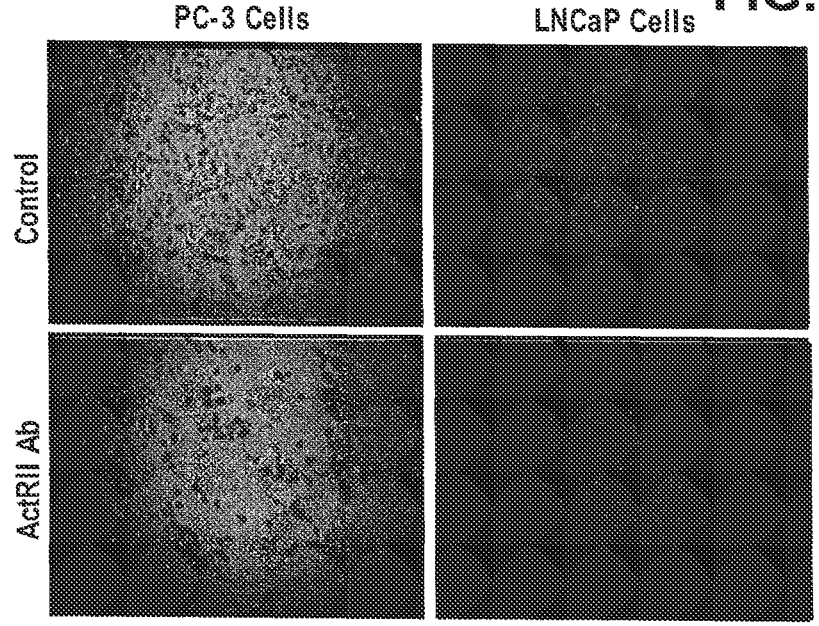
Figure 2F:
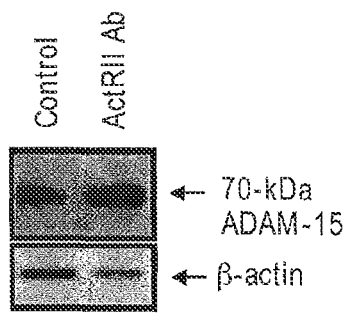
Figure 4A:
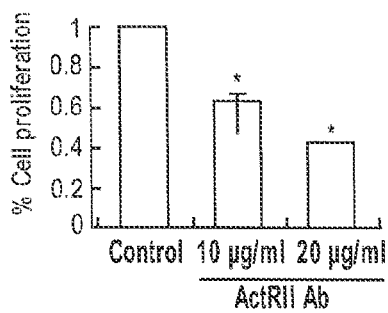
FIG. 4 illustrates that suppressing ActRII signaling promotes morphological changes, increased detachment and decreased viability of prostate cancer cells.
Figure 4B:
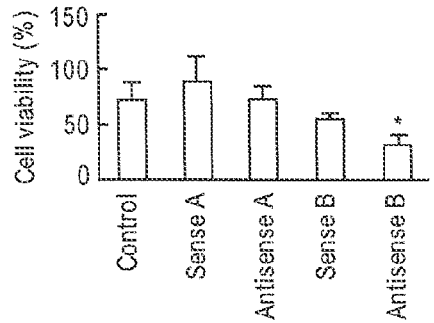
Figure 4C:
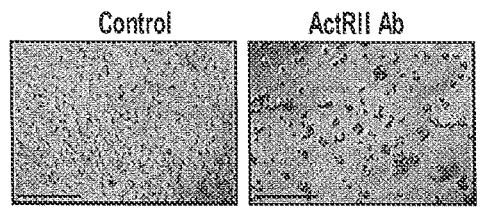
Figure 4D:
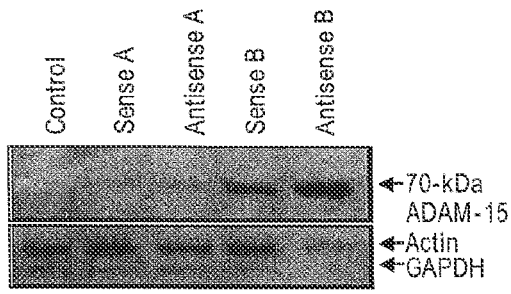
Figure 4D:
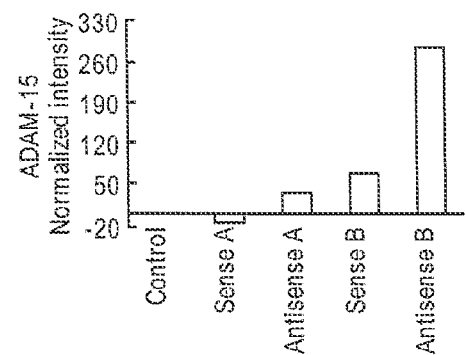

The present invention is described herein using several definitions, as set forth below and throughout the application.

As used in this specification and the claims, the singular forms "a," "an," and "the" include plural forms unless the content clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the term "including" has the same meaning as the term "comprising."

As used herein, the term "cancer cell line" or "cancer cells" may be used interchangeably and refers to cells isolated from a tumor, metastasis or abnormal growth derived from an animal or human. These cells typically, but not always, grow rapidly in culture when supplemented with appropriate growth factors, often fetal animal serum. This term also refers to normal cells transformed into cells that display typical features of cancer cells, i.e. they divide in cell culture under trophic support and/or form tumors when administered to animals.

Cancer cell lines may include, but are not limited to, human prostate cancer cells (PC-3, LNCaP, DU-145), human mammary epithelial cells (e.g. MCF-7, MCF-10A, MDA-MB-438, MDA-231, MDA-468, T47D, SkBr3), human neuronal cells (M17, SHSYSY, H4, U87), human acute myeloid leukemia cells (THP-1), human bone cancer cells (Saos-2 cells), human melanoma cells (721), human glioblastoma cells (A172), human head and neck carcinoma cells (A253), human skin epithelial cells (A431), human lung carcinoma epithelial cells (A-549), human peripheral blood mononuclear cell lymphoma (BCP-1), human pancreatic adenocarcinoma cells (BxPC3), human squamous cell carcinoma (Cal-27), human CML acute phase T cell leukemia cells (CML T1), human CML blast crisis Ph+ CML cells (EM2), human CML blast crisis Ph+ CML cells (EM3), human metastatic lymph node melanoma cells (FM3), human lung cancer cells (H1299), human hybridoma cells (HB54), human fibroblasts (HCA2), human kidney embryonic epithelial cell (HEK-293), human cervical cancer epithelial cell (HeLa), human myeloblast blood cells (HL-60), human mammary epithelial cells (HMEC), human colon epithelial adenocareinoma cells (HT-29), human umbilical cord vein endothelial cells (HUVEC), human T-cell-leukemia white blood cells (Jurkat), human lymphoblastoid EBV immortalized B cells (JY cells), human lymphoblastoid CML blast crisis cells (K562 cells), human lymphoblastoid erythroleukemia cells (Ku812), human lymphoblastoid CML cells (KCL22), human lymphoblastoid AML cells (KG1), human lymphoblastoid CML cells (KY01), human melanoma cells (Ma-Mel 1, 2, 3 through 48), human WBC myeloid metaplasia AML cells (MONO-MAC 6), human T cell leukemia (Peer), human osteosarcoma cells (Saos-2), human T cell leukemia/B cell line hybridoma (T2), human colorectal carcinoma/lung metastasis epithelium cells (T84), human colorectal adenocarcinoma cells (HCT-15, HT-29), human monocyte AML cells (THP1), human glioblastoma-astrocytoma epithelial cells (U373), human glioblastoma-astrocytoma epithelial-like cells (U87), human leukemic monocytic lymphoma cells (U937), human lymphoblastoid cells (WT-49), human B-cell EBV transformed cells (YAR), human breast adenocarcinoma cells (NCI/ADR-RES. MDA-MB-231), human CNS glioblastoma cells (SF-268), human ovary adenocarcinoma cells (SK-OV-3), human lung carcinoma cells (NCIH460), human lung adenocarcinoma cells (A549), human liver carcinoma cells (Hep3B), human uterine sarcoma-drug sensitive cells (MES-SA), human uterine sarcoma—drug resistant cells (MES-SA/DX5), human skin primary melanoma cells (WM39), ape-kidney fibroblast cells (COS-7), African green monkey kidney epithelial cells (Vero cells), murine brain/cerebral cortex endothelial cells (bEnd.3), murine embryonic mesenchymal cells (C3H-10T1/2), murine T cell leukemia ECACC cells (EL4), marine embryonic fibroblasts (NIH-3T3), murine embryonic calvarial cells (MC3T3), murine hepatoma epithelial cell (Hepal cic7), marine adenocarcinoma cells (MC-38), murine epithelial cells (MTD-1A), murine endothelial cells (MyEnd), murine renal carcinoma cells (RenCa), murine melanoma cells (X63), murine lymphoma cells (YAC-1), murine T cell tumor cells (RMA/RMAS), murine breast adenocarcinoma cells (4T1), murine mammary normal epithelial cells (NmuMG), rat glioblastoma cells (9L), rat neuroblastoma cells (B35), canine mammary tumor cells (CMT), canine osteosarcoma cells (D17), canine histiocytosismonocyte/macrophages (DH82), rat pheochromocytoma cells (PC-12), rat pituitary tumor (GH3), canine kidney epithelial cells (MDCK II), murine B lymphoma B cells (lymphocyte A20), murine hone marrow stromal cells (ALC), murine melanoma cells (B16), murine colorectal carcinoma cells (CT26), baby hamster kidney fibroblasts (BHK-21), Asian tiger mosquito larval tissue (C6/36), insect-ovary cells (Sf-9), Chinese hamster ovary cells (CHO), onyvax prostate cancer cells (OPCN, OPCT), tobacco cells (BY-2), zebratish cells (ZF4 and AB9), Madin-Darby Canine Kidney (MDCK) epithelial cells, Xenopus kidney epithelial cells (A6).

As used herein, the term "primary cells" refers to cells isolated from tissues of animals.

Primary cells include, but are not limited to, keratinizing epithelial cells, wet stratified barrier epithelial cells, exocrine secretory epithelial cells, holinone secreting cells, metabolism and storage cells, barrier function cells of lung, gut, exocrine glands and urogenital tract, kidney cells, epithelial cells lining closed internal body cavities, ciliated cells, extracellular matrix secretion cells, blood and immune system cells, cells of the nervous system, autonomic neuron cells, sense organ and peripheral neuron supporting cells, central nervous system neurons and glial cells, lens cells, pigment cells, germ cells, nurse cells, interstitial cells, stem cells and other cells (see Appendix 1 for list of cells).

A "cell array" refers to a substrate comprising a plurality of cancer or primary cell lines.

The present methods and kits may utilize cell arrays to test agents for cell adhesion, cell invasion and cell viability.

The term "oligonucleotide" or "siRNA" refers to a nucleic acid sequence or fragments or portions thereof, which may be single or double stranded, and represents the sense or antisense strand. A oligonucleotide may include DNA or RNA, and may be of natural or synthetic origin. For example, a oligonucleotide or siRNA may include cDNA or in RNA. Oligonucleotides may include nucleic acid that has been amplified (e.g., using polymerase chain reaction). The oligonucleotide may contain phosphorothicate bonds.

The term "oligonucleotide" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. Oligonucleotides of the method which function as antisense oligonucleotides are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. An oligonucleotide antisense sequence) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. Oligonucleotides used as antisense oligonucleotides for specifically inactivating gene transcription or translation are capable of specifically hybridizing to the target gene.

The present methods and kits may utilize oligonucleotides. The term "antisense" and "sense" are complimentary to "antisensc oligonucleotide" and "sense oligonucleotide", respectively, and refers to an oligonucleotide that hybridizes to a target nucleic acid and is capable of specifically hybridizing to the target nucleic acid. Antisense or sense may be fully complementary to a target nucleic acid sequence or partially complementary. The level of complementarity will depend on many factors based, in general, on the function of the antisense or sense oligonucleotide. An antisense oligonucleotide can be used, for example to prevent gene transcription and translation for the formation of proteins. A sense oligonucleotide does not prevent gene transcription and translation for the foil-nation of proteins. Antisense and sense oligonucleotides can be labeled or unlabeled, or modified in any of a number of ways well known in the art. An antisense and sense oligonucleotides may specifically hybridize to a target nucleic acid.

As used herein, a "target nucleic acid" refers to a nucleic acid molecule containing a sequence that has at least partial complementarity with a target DNA/RNA sequence. A target DNA/RNA may specifically hybridize to a target nucleic acid.

As used herein, an "inhibitor" refers to a molecule that blocks or decreases the function, phosphorylation or translocation of a protein or the binding of a protein to another.

An "amino acid sequence" refers to a polypeptide or protein sequence.

The term "blocking antibody" refers to an antibody that blocks normal signaling by that protein, usually by binding to a particular amino acid sequence of that protein.

As used herein, the term "agent," which may be used interchangeably with the terms "chemical", "inhibitor" or "drug," refers to any compound that can be applied to cells.

As used herein, the term "chemical library" means a group of distinct drugs and drug classes maintained as a group that are tested individually or in combination for their ability to affect a cellular change, e.g. cell adhesion.

As used herein, the term "assay" or "assaying" means qualitative or quantitative analysis or testing.

As used herein, the term "cell viability" refers to whether a cell is living or dead. Cell viability measurements may be used to evaluate the death or life of cells. Cell viability tests can be used to determine the effectiveness of agents to promote life, or induce death.

As used herein, the term "cell invasion" and "migrate" refers to the ability of a cell to move from its starting position to a new place, under the influence of chemotaxis agents or not.

As used herein, the term "cell attachment" and "cell adhesion" refers to cell binding to a substrate, including but not limited to plastic and other substrates referred to in and the like.

As used herein, the term "ADAM-15 expression and function" refers to the concentration of ADAM-15 protein, and the activity of that protein to act as a metalloproteinase to cleave ECM proteins. More particularly, the term ADAM-15 refers to a disintegrin and metalloproteinase domain-containing protein 15.

As used herein, the term "ActRI, Smad-2 and Smad-4 expression and phosphorylation" refers to the concentrations of ActRI, Smad-2 and Smad-4, and whether ActRI, Smad-2 and Smad-4 are phosphorylated.

As used herein, the term "ActRII binding to ALKs" refers to the binding of one member of the ActRII family of proteins to another member of the ALK family of proteins.

As used herein, the term "Smad-2:Smad-4 coupling" refers to the binding of Smad2 to Smad-4 as a complex.

DETAILED DESCRIPTION

In some embodiments, the methods include: (a) using cancer cell lines and primary cells; (b) attaching cells to a matrix; (c) inducing detachment of cancer cells or primary cells by blocking the ActRII signaling pathway using oligonucleotides, oligonucleotides with phosphorothioate bonds (antisense-P phospho-oligonucleotides), siRNA, blocking antibodies, or inhibitors of protein function, binding or translocation; (d) using agents from chemical libraries or other agents; (e) measuring cell attachment; (f) measuring cell invasion; (g) measuring cell viability; (h) measuring the expression and activity of disintegrins, (i) measuring ActRII, activin receptor-like kinases (ALKs) 1-7, Smad-2, Smad-3 and Smad-4 expression and their phosphorylation; measuring ActRII binding to ALKs; (k) measuring Smad-2:Smad-4 coupling and translocation to the nucleus. In one method, cancer cell lines are induced to detach from a culture or microwell plate and agents are tested to determine their ability to prevent detachment and cell invasion.

In a preferred embodiment, the determination of the ability of the agent to inhibit cell detachment is made by treating cultured cancer cells with antisense-P phosphooligonucleotides and then treating the cells with chemical agents and measuring cell detachment, invasion, morphology and viability.

In some embodiments, the methods may include using plastic culture plates, or plastic culture plates that are coated with different binding substrates, including but not limited to fibronectin, vitronectin, bovine serum albumin, gelatin, Matrigel, fibrous matrix proteins (such as collagen I, collagen IV), fibrinogen, non-collagenous components (such as laminin molecules; GTFALRGDNGDNGQ (SEQ ID NO 7)—portion of the laminin alpha-chain), proteoglycans (such as chondroitin sulfate, dermatan sulfate, heparin, heparan sulfate and keratan sulfate, syndecans, perlecan), non-sulfated glycosaminoglycan (such as hyaluronan), entactin, core proteins (such as lumican, keratocan, mimecan, fibromodulin, PRELP, osteoadherin and aggrecan), dystroglycan glycoprotein complex and Lutheran blood group glycoprotein. Plates may consist of one or more wells (e.g. 6-, 12-, 24-, 48-, 96-, 384-well) for high throughput screening of agents.

In some embodiments, the methods may include using any cancer cell line that can adhere to the surface of the plate.

In some embodiments, the methods may include using any primary cells from animals, or human cells from biopsies, that can adhere to the surface of the plate.

In some embodiments, the methods may include using, but are not limited to oligonucleotides, oligonucleotides with phosphorothioate bonds, RNA interference (RNAi) or inhibitors for decreasing the expression or function of the activin signaling pathway including ActRIIA and B, activin receptor-like kinases (ALKs 1-7), Smad-2, Smad-3, Smad-4, activins (A, B, C, D and E). In another embodiment, the methods may include using blocking antibodies against members of the activin signaling pathway including ActR11, ActRI, Smad-2, Smad-4, activins (A, B, C, D and B), for decreasing protein function. In another embodiment, the methods may include using oligonucleotides, oligonucleotides with phosphorothioate bonds, RNAi or inhibitors to decrease phosphorylation of activin signaling pathway members. In another embodiment, the methods may include using oligonucleotides, oligonucleotides with phosphorothioate bonds, RNAi or inhibitors to inhibit ActRIIA and/or ActRIIB binding to ALKs 1-7. In another embodiment, the methods may include using oligonucleotides, oligonucleotides with phosphorothioate bonds, RNAi or inhibitors to decrease Smad-2:Smad-4 translocation to the nucleus. In another embodiment, the methods may include natural cellular inhibitors of the signal transduction pathway of ActRII signaling such as inhibin and follistatin.

The treatments may include single agents, combinations of agents or no agents. The treatments also may include solutions used to dissolve the agents.

Cell detachment and adhesion may be detected by any suitable method, which may include, but are not limited to, cell cytometry (e.g. trypan blue), fluorescent based cell detection assays (e.g. Calcein AM (InVitrogen, Inc.), and Mitotracker Red (InVitrogen, Inc.), luminescent based detection assays (e.g. Cell-Titer glo (Promega, Inc.) and spectrophotometry based detection assays (e.g. crystal violet, MTS/MTT assays such as Promega CellTiter 96® AQueous Non-Radioactive Cell Proliferation Assay, Promega, Inc. and Chemicon Cell Adhesion Assays).

Cell invasion may be detected by any suitable method, which may include, but are not limited to, the scratch wound assay, cell invasion assays using fluorescent detection of cell invasion (e.g. activin, serum) (BD BioCoat matrigel invasion chambers, Fisher Scientific; EMD, Calbiochem; Chemicon international) with or without the use of a chemotaxic agent.

Cell viability may be detected by any suitable method, which may include, but are not limited to, cell cytometry (e.g. trypan blue), fluorescent based cell detection assays (e.g. calcein AM (InVitrogen, Inc.), and Mitotracker Red (InVitrogen, Inc.)), luminescent based detection assays (e.g. Cell-Titer glo (Promega, Inc)) and spectrophotometry based detection assays (e.g. crystal violet, MTS/MTT assays such as Promega CellTiter 960 AQueous Non-Radioactive Cell Proliferation Assay, Promega, Inc.)

Cell morphology may be assessed by capturing images using a microscope and analyzing morphological changes using software such as MetaMorph (Molecular Devices).

The disclosed methods will determine which agents or combination of agents prevent cell detachment, prevent cell invasion, promote cell attachment, promote cell invasion, increase viability, decrease viability and alter morphology.

The disclosed methods may be utilized to identify agents that: 1) prevent metastasis or the other conditions/diseases such as those described; 2) detach cells from a matrix; and 3) promote cell adhesion to a matrix. In addition, the disclosed methods may be utilized to study cell surface markers during cell detachment and how agents affect the expression and activity of those markers. Also contemplated are kits for performing the disclosed methods. A kit may include, one or more reagents for determining, either directly or indirectly, whether an agent(s) can prevent cell detachment, prevent cell invasion, promote cell attachment, promote cell invasion and alter morphology/viability.

The present methods may be performed to induce cell detachment from a matrix and to identify agents that prevent cell detachment. Cells are cultured to attain 80% confluence as known in the art. Typically cells are cultured under sterile conditions at 37° C., 5% CO2, in media supplemented with 1% penicillin-streptomycin, 2 mM glutamine, 0.4 mM sodium bicarbonate and 1-10% fetal bovine serum as determined by the cell type and as known in the art. Cells are then treated with antisense oligonucleotides with phosphorothioate bonds or RNAi to a final concentration of 0.1-10 μM.

Oligonucleotides can be added directly, or added to media that has been preincubated with lipofectamine (4 ng/ml; InVitrogen Corporation, Carlsbad, Calif.) for 5 min. at room temperature, and this mixture then incubated at room temperature for 20 min. prior to addition to cells, Cell attachment, invasion and viability are significantly altered by suppressing ActRII signaling via these treatments. Agent(s) are then added to cells at concentrations ranging from picomolar to millimolar concentrations. Fluids that the agent(s) are dissolved in are added to separate wells at the same concentration. Other control wells contain no agent(s). After 0-5 days of treatment, cell attachment, invasion, morphology and viability are measured as described.

The ability of agents to prevent cell detachment is measured by the difference in cell attachment between those cells treated with and without agents. Alternatively, the percentage change in cell attachment by an agent can be measured by the level of cell attachment in the presence of the agent and oligonucleotides or blocking antibody divided by the difference between cells treated with and without oligonucleotides/ or antibody alone as known in the art.

Cell detachment can be induced by, but is not limited to, the following oligonucleotides:

```
ActRIIA antisense-P:
                                    SEQ ID NO 1
5'-TCCAGTTCAGAGTCCCATTTC-3'

ActRIIA sense:
                                    SEQ ID NO 2
5'-GAAATGGGACTCTGAACTGGA-3'

ActRIIB antisense-P:
                                    SEQ ID NO 3
5'-TCTCCCGTTCACTCTGCCAC-3'

ActRIIB sense:
                                    SEQ ID NO 4
5'-GTGGCAGAGTGAACGGGAGA-3'

ADAM-15 Antisense-P:
                                    SEQ ID NO 5
5'-CGCACTCTTCCCTGGTAGCA-3'

ADAM-15 Sense:
                                    SEQ ID NO 6
5'-TGCTACCAGGGAAGAGTGCG-3'
```

Cell detachment can be induced by, but is not limited to, the following antibodies and inhibitors: Anti-human ActRIIB affinity-purified mouse monoclonal antibody (A0856; US Biological, Swampscott, Mass.); Anti-human mouse activin antibody (US Biologicals, MA): SB 431542 (GlaxoSmithKline). Any oligonucleotide or antibody that decreases signaling via the ActRII signaling pathway can be used to induce cell detachment.

The present methods may be performed to identify agents that promote cell attachment and prevent cell detachment from a matrix. Cells cultured as described at 50% confluence are treated with and without agents and after 0-5 days cell attachment, invasion and viability are measured in any suitable manner. Specific examples of suitable methods of measuring cell attachment, invasion and viability include thus methods described.

The present methods may be used for identifying agents that prevent cell detachment and promote cell adhesion. These agents may be used to treat any suitable metastasis and other diseases and conditions. Specific examples of suitable metastasis and other diseases and conditions include those described.

In a particular embodiment of the invention, a kit for identifying agent that prevent ActRII-mediated cell detachment is provided. The kit may include any suitable reagents for performing various assays capable of identifying agent that prevent ActRII-mediated cell detachment. In a particular example, the kit includes:
1) sense and antisense-P oligonucleotides to ActRII
2) lipofectamine
3) 96-well plate (coated with a particular matrix for different cell types). Plate would be either visible, fluorescent of luminescent light compatible. Celts would be dependent upon each researchers requirements as would the media that they would put the lipofectamine/oligonucleotides into for treatment of cells.
4) PBS buffer (for washing wells)
5) cell detection reagents In addition, depending upon the cell number detection method, the kit may include various additional reagents for performing particular assays such as, for example, fluorescent detection of cell number, luminescent detection of cell number, spectrophotometric detection of cell number, and the like. For fluorescent detection of cell number, the kit may include reagents for calcein AM (e.g., fluorescent compatible 96-well plate). For luminescent detection of cell number, the kit may include reagents for CellTiter-Glo® (e.g., luminescent compatible 96-well plate). For spectrophotometric detection of cell number, the kit may include reagents for crystal violet assay such as:
1) PBS buffer (for washing wells)
2) crystal violet solution (0.5%; staining cells)
3) 33% (v/v) acetic acid (digesting cells)
4) (visible light compatible 96-well plate)

To perform the spectrophotometric detection of cell number: Media is removed from cells cultured in 96-well plates, the cells washed with D-PBS (Gibco, Carlsbad, Calif., USA), and 504, of crystal violet added to each well at room temperature for 10 min. Following this, 200 uL of 33% (v/v) acetic acid is added to the wells, the plate shaken for 2 min. and then read at 570 nm on a plate reading spectrophotometer.

Methods and Results

EXAMPLE 1

ActRII Oligonucleotide-induced Detachment of Cancer Cells in a Microwell Format for the High Throughput Screening of Small Molecules to Inhibit Cell Detachment Prostate cancer cell lines (e.g. PC-3 cells) are cultured in 96-well opaque plates (luminescence compatible) at 37° C. in 100 μL of F-12 Nutrient Mixture (Ham; Gibco, InVitrogen Corporation, Carlsbad, Calif.) supplemented with 1% penicillin-streptomycin (P/S; Gibco, InVitrogen), 2 mM glutamine (InVitrogen), 0.4 mM sodium bicarbonate (Sigma, St. Louis, Mo.), and 5% fetal bovine serum (FBS, #26400-036; Gibco, InVitrogen). When cells reach 80% confluence (at least 24 h after plating to allow suitable attachment), cells are treated every day for 1-3 days with:
1) medium+0.4 μM ActRIIB sense-P oligonucleotide (SEQ ID NO 4); or
2) medium+0.4 μM ActRIIB antisense-P oligonucleotide (SEQ ID NO 3); or
3) medium+0.4 μM ActRIIB antisense-P oligonucleotide (SEQ ID NO 3)+small molecule (0-10 μM).
4) medium+0.4 μM ActRIIB sense-P oligonucleotide (SEQ ID NO 4)+small molecule (0-10 μM).

The oligomers with phosphorothioate bonds (sense and antisense-P; integrated DNA Technology, Coralville, Iowa) are added to media that has been preincubated with lipofectamine (4 ng/µl; InVitrogen Corporation, Carlsbad, Calif.) for 5 min. at room temperature. This mixture is incubated at room temperature for 20 min. prior to addition to cells. Replicates=3-6. As a modification to the above protocol, antisense oligonucleotides can be replaced with a specific binding antibody to ActRII such as anti-human ActRIIB affinity-purified mouse monoclonal antibody (A0856; US Biological, Swampscott, Mass.).

The number of viable cells attached to the plate is determined using the CellTiter-Glo® Luminescent Cell Viability Assay (Promega). Briefly, the CellTiter-Glo® Reagent is added directly to the wells of the plate (100 µL per well for 96-well plates) and the plate mixed on an orbital shaker for 2 min. Following this, the plate is incubated at room temperature for 10 min. and the luminescence recorded (typical integration time of 0.25-1 second per well) on a plate-reading luminometer. Note: Control wells are prepared containing medium without cells to obtain a value for background luminescence, and is subtracted from the values obtained for cells treated in 1, 2 and 3 above.

The % of cell detachment rescued by the small molecules is determined as the luminescence of (3-2)/(1-2) x100.

Example 2

Figure 5:
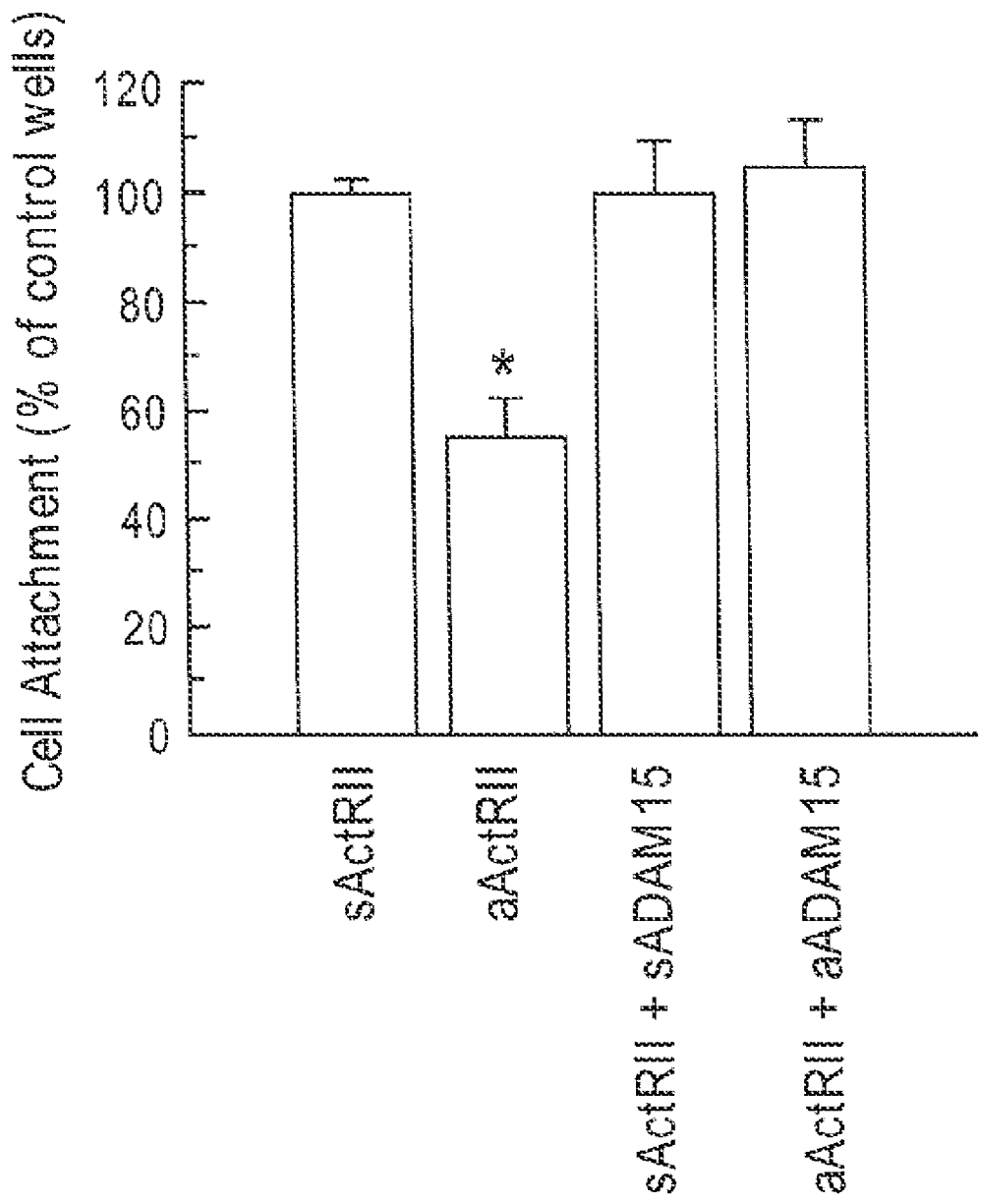
FIG. 5 illustrates antisense oligonucleotide suppression of ActRII along with ADAM 15 suppression to prevent cell detachment.

Antisense Oligonucleotide Suppression of ActRII along with ADAM-15 Suppression Prevents Cell Detachment To test that cell detachment induced by suppressing ActRII signaling was mediated via the metalloprotease ADAM-15, we treated PC-3 prostatic cancer cells with antisense-P against ActRII and then treated these cells with antisense-P against ADAM-15. A significant decrease in cell attachment was detected after 3 days of treatment with antisense-P against ActRII, and this was reversed by treatment with antisense-P against ADAM-15 ($p<0.01$, n 5). As shown in FIG. 5, neither sense against ActRII nor together with sense against. ADAM-15 altered cell attachment. These results illustrate that cell detachment induced by suppressing ActRII signaling is mediated via the metalloprotease ADAM-15, and further indicate that antisense-P against ADAM-15 as a chemical that can prevent prostate cancer cell detachment.

Androgen-insensitive PC3 cells derived from a grade IV human prostate adenocarcinoma of epithelial origin (examples described herein) were maintained at 37° C. in F-12 Nutrient Mixture (Ham; Gibco, InVitrogen Corporation, Carlsbad, Calif.) supplemented with 1% penicillin-streptomycin (P/S; (Gibco, InVitrogen), 2 mM glutamine (InVitrogen), 0.4 mM sodium bicarbonate (Sigma, St. Louis, Mo.), and 5% fetal bovine serum (FBS, #26400-036; Gibco, InVitrogen). For the experiment, PC-3 cells were plated in 6 well plates with 10% serum at $2\times10^5$ cells/well for 24 h, after which cells treated every day for 3 days with:
1) media containing 10% serum+lipofectamine+sense-P oligonucleotide to ActRIIB (sActRIIB) (SEQ ID NO 4);
2) media containing 10% serum+lipofectamine+antisense-P oligonucleotide to ActRBB (aActRIIB) (SEQ ID NO 3);
3) media containing 10% serum+lipofectamine+sense-P oligonucleotide to ActRIIB (sActRIIB) (SEQ ID NO 4)+sense-P oligonucleotides to ADAM-15 (SEQ ID NO 6)
4) media containing 10% serum+lipofectamine+aActRIIB (SEQ ID NO 3)+antisense-P oligonucleotides to ADAM-15 (SEQ ID NO 5).

The oligomers with phosphorothioate bonds (Sense and antisense-P; Integrated DNA Technology, Coralville, Iowa) were added to media (240 µl) that had been preincubated with lipofectamine (4 ng/µl; InVitrogen Corporation, Carlsbad, Calif.) for 5 min, at room temperature. This mixture was then incubated at room temperature for 20 min. prior to addition to cells. Antisense-P was used at a final concentration of 0.4 µM. The number of viable PC-3 cells attached to the plate was measured after trypsinization followed by cell counting using the trypan blue staining assay at the end of 72 h. Results are presented as cell attachment (% of sense control; mean±SEM, n=5), Statistical differences are denoted by an * $p<0.01$ as shown in FIG. 5. In addition to the methods and results presented herein, methods and results described in "Simon D, Vadakkadath Meethal S. Wilson A C, et al, Activin receptor signaling regulates prostatic epithelial cell adhesion and viability. Neoplasia 11:365-376" the disclosure of which is incorporated herein in its entirety.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

| Sequence Listing | |
|---|---|
| ActRIIA antisense-P: 5'-TCCAGTTCAGAGTCCCATTTC-3' | SEQ ID NO 1 |
| ActRIIA sense: 5'-GAAATGGGACTCTGAACTGGA-3' | SEQ ID NO 2 |
| ActRIIB antisense-P: 5'-TCTCCCGTTCACTCTGCCAC-3' | SEQ ID NO 3 |
| ActRIIB sense: 5'-GTGGCAGAGTGAACGGGAGA-3' | SEQ ID NO 4 |
| ADAM-15 Antisense-P: 5'-CGCACTCTTCCCTGGTAGCA-3' | SEQ ID NO 5 |
| ADAM-15 Sense: 5'-TGCTACCAGGGAAGAGTGCG-3' | SEQ ID NO 6 |
| laminin molecules GTFALRGDNGDNGQ | SEQ ID NO 7 |

REFERENCES

1. Podsypanina. K, Du Y C, Jechlinger M, Beverly L J, Hambardzutnyan D, Varmus H 2008 Seeding and propagation of untransformed mouse mammary cells in the lung. Science 321:1841-4
2. Klein C A 2008 Cancer. The metastasis cascade. Science 321:1785-7
3. Chiang A C, Massague J 2008 Molecular basis of metastasis. N Engl Med 359:2814-23
4. Simon D, Vadakkadath Meethal S, Wilson A C, et al. 2009 Activin receptor signaling regulates prostatic epithelial cell adhesion and viability. Neoplasia 11:365-376

5. Rocks N, Paulissen G, El Hour M, et al. 2007 Emerging roles of ADAM and ADAMTS metalloproteinases in cancer. Biochimie
6. Najy A J, Day K C, Day M L 2008 ADAM15 supports prostate cancer metastasis by modulating tumor cell-endothelial cell interaction. Cancer Res 68:1092-9
7. Kuefer R, Day K C, Kleer C G, et al. 2006 ADAM15 disintegrin is associated with aggressive prostate and breast cancer disease. Neoplasia 8:319-29
8. Yamada D. Ohuchida K, Mizumoto K, et al. 2007 Increased expression of ADAM 9 and ADAM 15 mRNA in pancreatic cancer, Anticancer Res 27:793-9
9, Martin J, Eynstone L V, Davies M, Williams J D, Steadtnan R 2002 The role of ADAM 15 in glomerular mesangial cell migration. J Biol Chem 277:33683-9
10. Charrier-Hisamuddin L, Laboisse C L, Merlin D 2007 ADAM-15: a metalioprotease that mediates inflammation. Faseb J
11, Jeruss J S, Sturgis C D, Rademaker A W, Woodruff T K 2003 Down-regulation of activin, activin receptors, and Smads in high-grade breast cancer. Cancer Res 63:3783-90
12, Guo Y, Jacobs S C, Kyprianou N 1997 Down-regulation of protein and mRNA expression for transforming growth factor-beta (TGF-beta1) type I and type II receptors in human prostate cancer, Int J Cancer 71:573-9
13. Leto G, Incorvaia L, Badalamenti C, et al. 2006 Aetivin A circulating levels in patients with bone metastasis from breast or prostate cancer. Clin Exp Metastasis 23:117-22
14. Kaighn M E, Lechner J F, Narayan K S, Jones L W 1978 Prostate carcinoma: tissue culture cell lines. Natl Cancer Inst Monogr: 17-21
15, Kaighn M E, Narayan K S, Ohnuki Y, Lechner J F, Jones L W 1979 Establishment and characterization of a human prostatie carcinoma cell line (PC-3), Invest Urol 17:16-23

Appendix 1

Keratinizing epithelial cells such as epidermal keratinocyte (differentiating epidermal cell), epidermal basal cell (stem cell), keratinocyte of fingernails and toenails, nail bed basal cell (stem cell), medullary hair shaft cell, cortical hair shaft cell, cuticular hair shaft cell, cuticular hair root sheath cell, hair root sheath cell of Huxley's layer, hair root sheath cell of Henle's layer, external hair root sheath cell, hair matrix cell (stein cell).

Wet stratified barrier epithelial cells such as surface epithelial cell of stratified squamous epithelium of cornea, tongue, oral cavity, esophagus, anal canal, distal urethra and vagina, nasal cell (stem cell) of epithelia of cornea, tongue, oral cavity, esophagus, anal canal, distal urethra and vagina, urinary epithelium cell (lining urinary bladder and urinary ducts).

Exocrine secretory epithelial cells such as salivary gland mucous cell (polysaccharide-rich secretion), salivary gland serous cell (glycoprotein enzyme-rich secretion), von Ebner's gland cell in tongue (washes taste buds), mammary gland cell (milk secretion), lacrimal gland cell (tear secretion), ceruminous gland cell in ear (wax secretion), eccrine sweat gland dark cell (glycoprotein secretion), eccrine sweat gland clear cell (small molecule secretion), apocrine sweat gland cell (odoriferous secretion, sex-hormone sensitive), gland of Moll cell in eyelid (specialized sweat gland), sebaceous gland cell (lipid-rich sebum secretion), Bowman's gland cell in nose (washes olfactory epithelium), Brunner's gland cell in duodenum (enzymes and alkaline mucus), seminal vesicle cell (secretes seminal fluid components, including fructose for swimming sperm), prostate gland cell (secretes seminal fluid components), bulbourethral gland cell (mucus secretion), Bartholin's gland cell (vaginal lubricant secretion), gland of Littre cell (mucus secretion), uterus endometrium cell (carbohydrate secretion), isolated goblet cell of respiratory and digestive tracts (mucus secretion stomach lining mucous cell (mucus secretion), gastric gland zymogenic cell (pepsinogen secretion), gastric gland oxyntic cell (hydrochloric acid secretion), pancreatic acinar cell (bicarbonate and digestive enzyme secretion), Paneth cell of small intestine (lysozyme secretion), type II pneumocyte of lung (surfactant secretion), Clara cell of lung.

Hormone secreting cells such as anterior pituitary cells, somatotropes, lactotropes, thyrotropes, gonadotropes, corticotropes, intermediate pituitary cell, secreting melanocyte-stimulating hormone, magnocellular neuroseqretory cells, cells secreting oxytocin, secreting vasopressin, gut and respiratory tract cells, secreting serotonin, secreting endorphin, secreting somatostatin, secreting gastrin, secreting secretin, secreting cholecystokinin, secreting insulin, secreting glucagon, secreting bombesin, thyroid gland cells, thyroid epithelial cell, parafollicular cell, parathyroid gland cells, parathyroid chief cell, oxyphil cell, adrenal gland cells, chromaffin cells, secreting steroid hormones (mineralcorticoids and gluco corticoids), leydig cell of testes secreting testosterone, theca interna cell of ovarian follicle secreting estrogen, corpus luteum cell of ruptured ovarian follicle secreting progesterone, granulosa lutein cells, theca lutein cells, juxtaglomerular cell (renin secretion), macula densa cell of kidney, peripolar cell of kidney, mesangial cell of kidney. Metabolism and storage cells such as hepatocyte (liver cell), white fat cell, brown fat cell, liver lipocyte.

Barrier function cells of lung, gut, exocrine glands and urogenital tract. Kidney cells such as kidney glomerulus parietal cell, kidney glomerulus podocyte, kidney proximal tubule brush border cell, Loop of Henle thin segment cell, kidney distal tubule cell, kidney collecting duct cell.

Epithelial cells lining closed internal body cavities such as blood vessel and lymphatic vascular endothelial fenestrated cell, blood vessel and lymphatic vascular endothelial continuous cell, blood vessel and lymphatic vascular endothelial splenic cell, synovial cell (lining joint cavities, hyaluronie acid secretion), serosal cell (lining peritoneal, pleural, and pericardial cavities), squamous cell (lining perilymphatic space of ear), squamous cell (lining endolymphatic space of ear), columnar cell of endolymphatic sac with microvilli (lining endolymphatic space of ear), columnar cell of endolymphatic sac without microvilli (lining endolymphatic space of ear), dark cell (lining endolymphatic space of ear), vestibular membrane cell (lining endolymphatic space of ear), stria vascularis basal cell (lining endolymphatic space of ear), stria vascularis marginal cell endolymphatie space of ear), cell of Claudius (lining endolymphatic space of ear), cell of Boettcher (lining endolymphatic space of ear), choroid plexus cell (cerebrospinal fluid secretion), pia-arachnoid squamous cell, pigmented ciliary epithelium cell of eye, nonpigmented ciliary epithelium cell of eye, corneal endothelial cell.

Ciliated cells with propulsive function such as respiratory tract ciliated cell, oviduct ciliated cell (in female), uterine endometrial ciliated cell (in female), rete testis ciliated cell (in male), ductulus efferens ciliated cell (in male), ciliated ependymal cell of central nervous system (lining brain cavities).

Extracellular matrix secretion cells such as ainelobiast epithelial cell (tooth enamel secretion), planum semilunatum epithelial cell of vestibular apparatus of ear (proteoglycan secretion), organ of Corti interdental epithelial cell (secreting tectorial membrane covering hair cells), loose connective tissue fibroblasts, corneal fibroblasts, tendon fibroblasts, bone marrow reticular tissue fibroblasts, other nonepithelial fibroblasts such as pericyte, nucleus pulposus cell of intervertebral disc, cementoblast/cementocyte (tooth root bonelike cementum secretion), odontoblast/odontocyte (tooth dentin secretion), hyaline cartilage chondrocyte, fibrocartilage chondrocyte, elastic cartilage chondrocyte, osteoblast/osteocyte, osteoprogenitor cell (stem cell of osteoblasts), hyalocyte of vitreous body of eye, stellate cell of perilymphatic space of ear contractile cells such as skeletal muscle cells, red skeletal muscle cell (slow), white skeletal muscle cell (fast), intermediate skeletal muscle cell, nuclear bag cell of muscle spindle, nuclear chain cell of muscle spindle, satellite cell (stem cell), heart muscle cells such as ordinary heart muscle cell, nodal heart muscle cell, purkinje fiber cell, smooth muscle cell (various types), myoepithelial cell of iris, myoepithelial cell of exocrine glands.

Blood and immune system cells such as erythrocyte (red blood cell), megakaryocyte (platelet precursor), monocyte, connective tissue macrophage (various types), epidermal Langerhans cell, osteoclast (in bone), dendritic cell (in lymphoid tissues), microglial cell (in central nervous system), neutrophil granulocyte, eosinophil granulocyte, basophil granulocyte, mast cell, helper cell, suppressor T cell, cytotoxic T cell, natural Killer T cell, B cell, natural killer cell, reticulocytes, stem cells and committed progenitors for the blood and immune system (various types).

Cells of the nervous system such as sensory transducer cells which include auditory inner hair cell of organ of Corti, auditory outer hair cell of organ of Corti, basal cell of olfactory epithelium (stem cell for olfactory neurons), cold-sensitive primary sensory neurons, heat-sensitive primary sensory neurons, merkel cell of epidermis (touch sensor), olfactory receptor neuron, pain-sensitive primary sensory neurons (various types), photoreceptor cells of retina in eye (Photoreceptor rod cells, photoreceptor blue-sensitive cone cell of eye, photoreceptor green-sensitive cone cell of eye, photoreceptor red-sensitive cone cell of eye), proprioceptive primary sensory neurons (various types), touch-sensitive primary sensory neurons (various types), type I carotid body cell (blood pH sensor), type II carotid body cell (blood pH sensor), type I hair cell of vestibular apparatus of ear (acceleration and gravity), type II hair cell of vestibular apparatus of ear (acceleration and gravity), type I taste bud cell.

Autonomic neuron cells such as cholinergic neural cell (various types), adrenergic neural cell (various types), peptidergic neural cell (various types).

Sense organ and peripheral neuron supporting cells such as inner pillar cell of organ of Corti, outer pillar cell of organ of Corti, inner phalangeal cell of organ of Corti, outer phalangeal cell of organ of Corti, border cell of organ of Corti. Hensen cell of organ of Corti, vestibular apparatus supporting cell, type I taste bud supporting cell, olfactory epithelium supporting cell, Schwann cell, satellite cell (encapsulating peripheral nerve cell bodies), enteric glial Central nervous system neurons and glial cells such as astrocyte (various types), neuron cells (large variety of types, still poorly classified), oligodendrocyte, spindle neuron.

Lens cells such as anterior lens epithelial cell, crystallin-containing lens fiber cell.

Pigment cells such as melanocyte, retinal pigmented epithelial cell.

Germ cells such as oogonium/oocyte, spermatid, spermatocyte, spermatogonium cell
(stem cell for spermatocyte), spermatozoon.

Nurse cells such as ovarian follicle cell, sertoli cell (in testis), thymus epithelial cell.

Interstitial cells like interstitial kidney cells.

Stem cells such as embryonic stem cells, mesenchymal stem cells, subcutaneous preadipocytes, visceral preadipocytes, osteoclast precursors, neural progenitors, bone marrow mononuclear cells, cord blood mononuclear cells, bone marrow progenitors, cord blood progenitors, cord blood erythroid progenitors, fetal liver progenitors, bone marrow stromal cells.

Other cells such as type I pneumocyte (lining air space of lung), pancreatic duet cell (centroacinar cell), nonstriated duct cell (of sweat gland, salivary gland, mammary gland, etc.), principal, cell, intercalated cell, duct cell (of seminal vesicle, prostate gland, etc.), intestinal brush border cell (with microvilli), exocrine gland striated duct cell, gall bladder epithelial cell, ductulus efferens nonciliated cell, epididymal principal cell, epididymal basal cell.

What is claimed is:

1. A kit to identify an agent to modify cell adhesion, the kit comprising:
   a cell growth media;
   a container having a surface matrix for cell adhesion; and
   a cell detachment solution having a concentration of an activin receptor II signaling suppressor sufficient to induce cell detachment.

2. The kit according to claim 1, further comprising:
   sense and antisense-P oligonucleotides to activin receptor II.

3. The kit according to claim 2, further comprising:
   DNA having the sequence of SEQ ID 3.

4. The kit according to claim 2, further comprising:
   DNA having the sequence of SEQ ID 4.

5. The kit according to claim 2, further comprising:
   DNA having the sequence of SEQ ID 5.

6. The kit according to claim 2, further comprising:
   DNA having the sequence of SEQ ID 6.

7. The kit according to claim 1, further comprising:
   lipofectamine.

8. The kit according to claim 1, further comprising:
   a 96-well microtiter plate for growing the cells.

9. The kit according to claim 1, further comprising:
   a cell detection reagent.

10. The kit according to claim 1, further comprising:
    a fluorescent cell detection reagent.

11. The kit according to claim 1, further comprising:
    a luminescent cell detection reagent.

12. The kit according to claim 1, further comprising:
    DNA having the sequence of SEQ ID 1.

13. The kit according to claim 1, further comprising:
    DNA having the sequence of SEQ ID 2.

14. The kit according to claim 1, further comprising:
    RNA interference (RNAi) molecules to activin receptor II.

15. The kit according to claim 12, further comprising:
    RNAi having the sequence of SEQ ID 3.

16. The kit according to claim 12, further comprising:
    RNAi having the sequence of SEQ ID 4.

17. The kit according to claim 1, further comprising:
    RNAi having the sequence of SEQ ID 1.

18. The kit according to claim 1, further comprising:
    RNAi having the sequence of SEQ ID 2.

19. The kit according to claim 1, further comprising:
    a cell detection reagent for spectrophotometry based detection assays.

\* \* \* \* \*

SEQUENCE LISTING

```
<160> NUMBER OF SEQ ID NOS: 7

<210> SEQ ID NO 1
<211> LENGTH: 21
<212> TYPE: DNA
<213> ORGANISM: Homo sapiens
<220> FEATURE:
<221> NAME/KEY: misc_feature
<223> OTHER INFORMATION: ActRIIA antisense

<400> SEQUENCE: 1
tccagttcag agtcccattt c                                            21

<210> SEQ ID NO 2
<211> LENGTH: 21
<212> TYPE: DNA
<213> ORGANISM: Homo sapiens
<220> FEATURE:
<221> NAME/KEY: misc_feature
<223> OTHER INFORMATION: ActRIIA sense

<400> SEQUENCE: 2
```

```
gaaatgggac tctgaactgg a                                              21

<210> SEQ ID NO 3
<211> LENGTH: 20
<212> TYPE: DNA
<213> ORGANISM: Homo sapiens
<220> FEATURE:
<221> NAME/KEY: misc_feature
<223> OTHER INFORMATION: ActRIIB antisense

<400> SEQUENCE: 3
tctcccgttc actctgccac                                                20

<210> SEQ ID NO 4
<211> LENGTH: 20
<212> TYPE: DNA
<213> ORGANISM: Homo sapiens
<220> FEATURE:
<221> NAME/KEY: misc_feature
<223> OTHER INFORMATION: ActRIIB sense

<400> SEQUENCE: 4
gtggcagagt gaacgggaga                                                20

<210> SEQ ID NO 5
<211> LENGTH: 20
<212> TYPE: DNA
<213> ORGANISM: Homo sapiens
<220> FEATURE:
<221> NAME/KEY: misc_feature
<223> OTHER INFORMATION: ADAM-15 Antisense

<400> SEQUENCE: 5
cgcactcttc cctggtagca                                                20

<210> SEQ ID NO 6
<211> LENGTH: 20
<212> TYPE: DNA
<213> ORGANISM: Homo sapiens
<220> FEATURE:
<221> NAME/KEY: misc_feature
<223> OTHER INFORMATION: ADAM-15 Sense

<400> SEQUENCE: 6
tgctaccagg gaagagtgcg                                                20

<210> SEQ ID NO 7
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of Laminin alpha-chain

<400> SEQUENCE: 7

Gly Thr Phe Ala Leu Arg Gly Asp Asn Gly Asp Asn Gly Gln
1               5                   10
```